United States Patent
Mückter (12)

(10) Patent No.: US 6,468,278 B1
(45) Date of Patent: Oct. 22, 2002

(54) IMPLANT FOR THE STABILIZATION OF A FRACTURE

(75) Inventor: Helmut Mückter, Aachen (DE)

(73) Assignee: Medos Medizintechnik GmbH, Stolberg (DE)

( * ) Notice: Subject to any disclaimer, the term of this patent is extended or adjusted under 35 U.S.C. 154(b) by 0 days.

(21) Appl. No.: 09/554,342

(22) PCT Filed: Nov. 5, 1998

(86) PCT No.: PCT/DE98/03303

§ 371 (c)(1),
(2), (4) Date: May 27, 2000

(87) PCT Pub. No.: WO99/25266

PCT Pub. Date: May 27, 1999

(30) Foreign Application Priority Data

Nov. 14, 1997 (DE) .......................... 197 50 493

(51) Int. Cl.$^7$ .............................................. A61B 17/80
(52) U.S. Cl. ............................ 606/69; 606/70; 606/73; 606/65
(58) Field of Search ................. 606/60, 65, 66, 606/67, 68, 69, 70, 71, 72, 73

(56) References Cited

U.S. PATENT DOCUMENTS

| | | |
|---|---|---|
| 2,612,159 A | 9/1952 | Collison |
| 4,465,065 A | 8/1984 | Gotfried |
| 4,488,543 A | * 12/1984 | Tornier |
| 4,657,001 A | 4/1987 | Fixel |
| 5,300,076 A | 4/1994 | Leriche |
| 5,693,055 A | 12/1997 | Zahiri et al. |

FOREIGN PATENT DOCUMENTS

| | | |
|---|---|---|
| DE | 33 01 298 | 2/1984 |
| DE | 92 00 328 | 2/1992 |
| EP | 0 337 288 | 4/1989 |
| FR | 2 606 268 | 11/1986 |

OTHER PUBLICATIONS

Osteosynthesis Traumatology Orthopaedics:, Nov. 1996, OSTEO AG, SELZACH, SCHWEIZ XP002096050 22291 "T-plates" vol. 1.14.

* cited by examiner

Primary Examiner—David O. Reip
(74) Attorney, Agent, or Firm—Collard & Roe, P.C.

(57) ABSTRACT

A plate provides guides for preferably two screws, which hold the screws in a stable way at an angle against the plate. Furthermore, the screws are preferably fixed in a stable and removable way with a clamping device against rotations around the screw barrel and shifts in the direction of the screw barrel. For this a special screw is suitable with an outer thread diameter, which is larger than the neighboring barrel diameter. To ensure a secure guidance, the barrel diameter is enlarged in the area of the screw head.

11 Claims, 6 Drawing Sheets

IMPLANT FOR THE STABILIZATION OF A FRACTURE

CROSS REFERENCE TO RELATED APPLICATIONS

Figure 1:
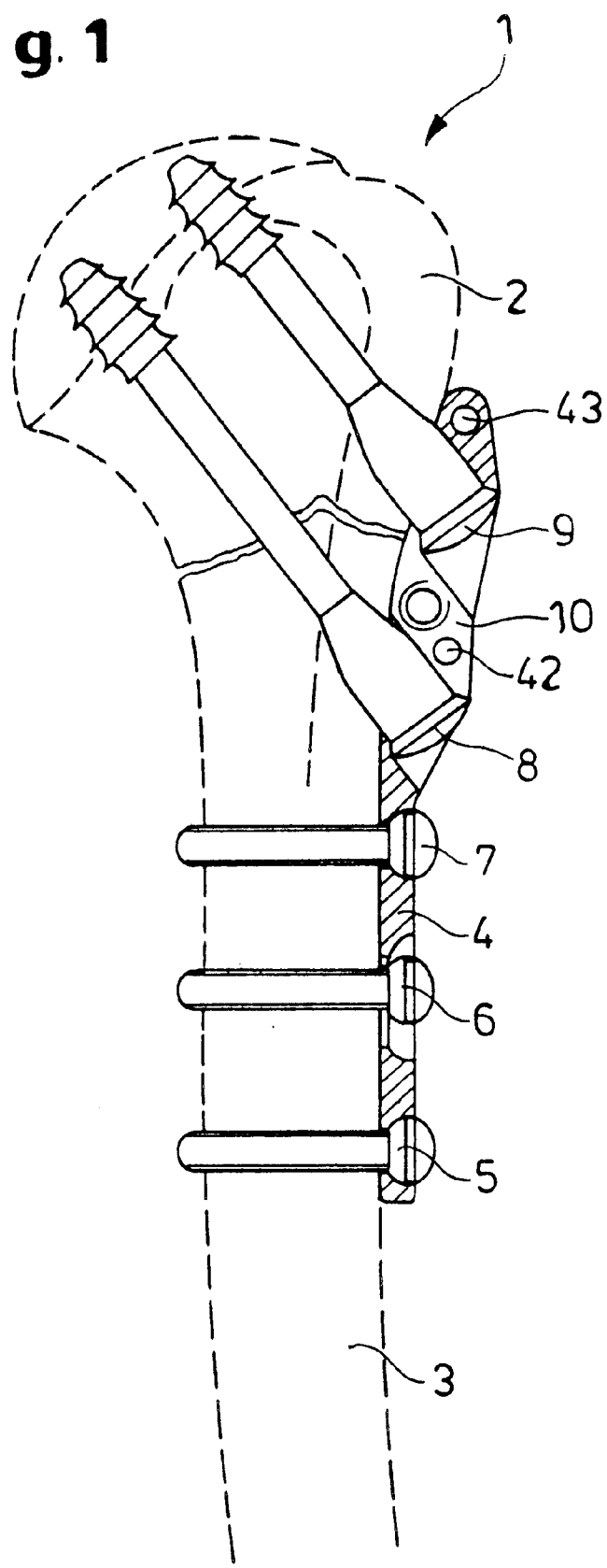

Applicant claims priority under 35 U.S.C. §119 of German Application No. 197 50 493.0 filed Nov. 14, 1997. Applicant also claims priority under 35 U.S.C. §120 of PCT/DE98/03303 filed on Nov. 5, 1998. The international application under PCT article 21 (2) was not published in English.

The invention concerns an implant for stabilization of a fracture of the humerus in the area of the head of the humerus with or without cooperation of the tubercula with a plate, in which holes for screws are provided, thus the plate provides a guide for a humerus head screw, which holds the humerus head screw in a stable way at an angle against the plate.

As a generic implant a disk for underlying and guiding is known from U.S. Pat. No. 5,693,055, which receives the forces at the screw head and by means of an increased contact surface on the shaft bone of the humerus achieves a reduced stress in the bone shaft. This guiding plate lies on the shaft bone rather like a washer disk and is fixed against the shaft bone only by the screw inserted into the humerus head. The function of the implant described in U.S. Pat. No. 5,693,055 consequently relies on the force of the screw in the humerus head and thus the inter-fragmentary compression generated, which, however, as experience shows, slackens within hours to days due to regularly occurring bone sintering.

A different implant is known from U.S. Pat. No. 4,657,001. This implant, however, is only suitable for the upper leg area and also leads to an inter-fragmentary compression.

The invention is therefore based on the task of further developing a generic implant, so that an easy, safe stabilization of the fracture can be achieved with it.

This task is solved by the plate providing a clamping device, which attaches the humerus head screws in a stable way against a shift in shaft direction and which is preferably removable. Such a clamping device blocks movements of the screw relative to the plate and consequently provides for an implant which holds rigidly, that cannot loosen even under strong movements of the upper arm.

When using two humerus head screws, not only is an angle-stable fixation of the head and shaft fragment of the bone against each other ensured, but also a rotation stability is achieved which prevents the loosening of the humerus head screws, e.g. during swinging excercises.

nAn application example provides, that the guides are part of the holes, the cross-sections of which correspond to a barrel diameter of the humerus head screws. These guides use the thickness of the plate, to hold the screws at an angle. To do this, the inner diameter of the hole is adjusted on at least one section of the hole exactly to the outer diameter of a barrel section of the screw, so that the screw can be inserted into the hole, but after this, can only be moved in the direction of the axis of the screw barrel. Although this configuration requires a certain thickness of the plate, it is, however, preferable for guides that project above the plate surface or to the contrary reach into the bone.

The angle pre-defined by the guides should approximately correspond with the angle of the humerus head. Therefore, an angle between 35° and 40° preferably 37.5° is proposed, measured against the longitudinal axis of the humerus shaft.

A preferred configuration of such a clamping device provides, that a gap with a cross hole is provided between the holes of the humerus head screws. A screw can be inserted into this cross hole in such a way that the gap is narrowed by tightening the screw. This causes the diameter of the holes to be slightly deformed and therefore to attach the humerus screws under retention of their angular position.

Preferably, the holes of the humerus head screws are arranged parallel to each other, so that their axes are in a single plane with the longitudinal axis of the humerus shaft. The axes of the humerus head screws consequently cross the longitudinal axis of the humerus shaft in the pre-defined angle at preferably 35°–40°. This arrangement of the screws on one line enables an operation with a very narrow exposure of the bone in the fractured area. This leads to a fast bone healing, because disturbances of the blood circulation are avoided.

To implement wire cerelages or PDS cords for re-attachment of a torn out tubercula, it is proposed to add holes on the plate running parallel to its upper and lower sides. These holes are to be preferably provided at the tip of the plate and in the area of the clamping device.

A preferred configuration of the plate is designed in a very compact way. This plate has a maximum length of 100 mm, a maximum width of 12 mm and its thickness is between 4 mm and 9.5 mm. A special design of the screw guide allows a maximum plate thickness of approximately 7 mm. In its shape the plate is adjusted to the anatomic conditions in the area of the proximal humerus. In the lower section the plate it is screwed with standard Corticalis screws at the proximal part of the humerus shaft. Due to the fact that in this area close to the joint no high bending moments occur, an attachment with three screws is sufficient. To cater for fractures, which reach into the humerus shaft area, the plate can also be designed longer with a correspondingly higher number of screw holes in the area of the humerus shaft.

Figure 2:
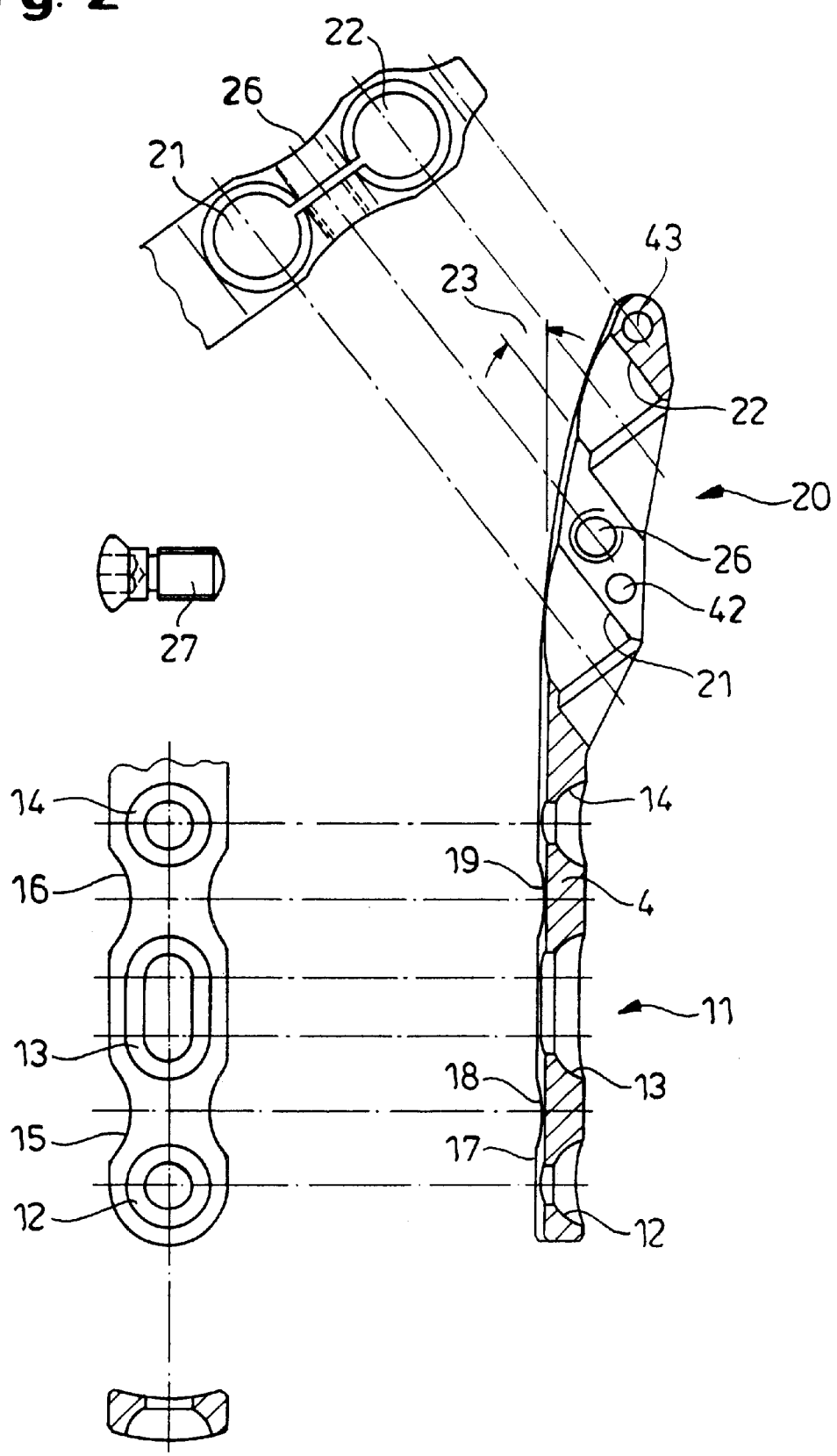
Figure 3:
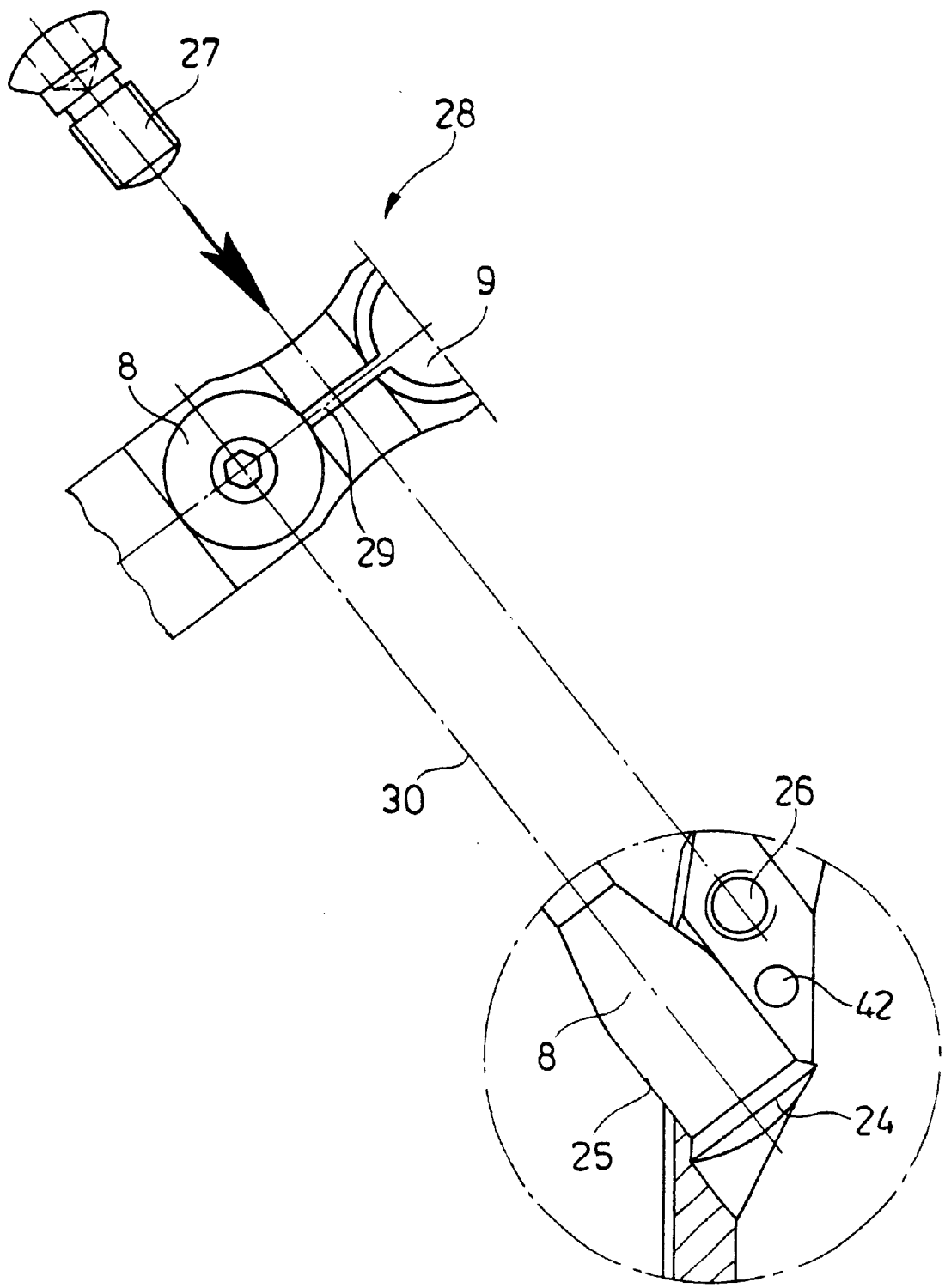
Figure 4:
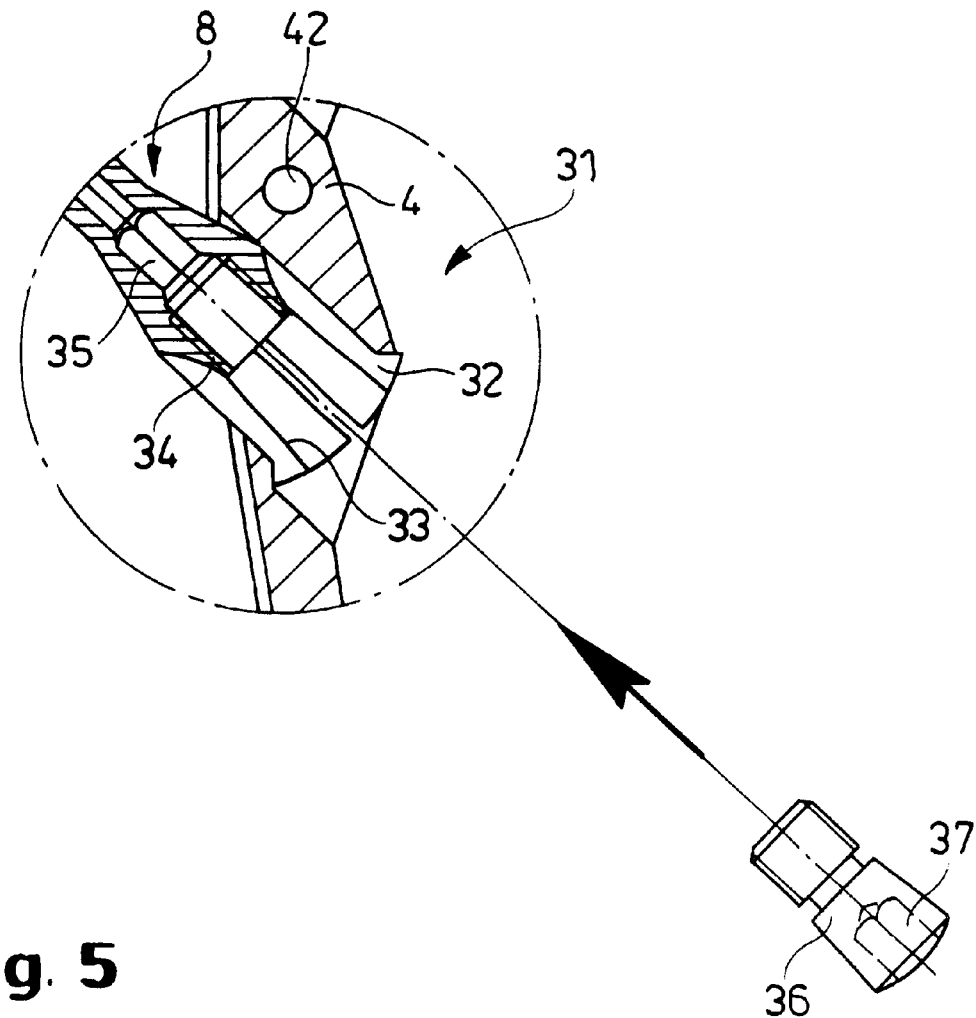
Figure 5:
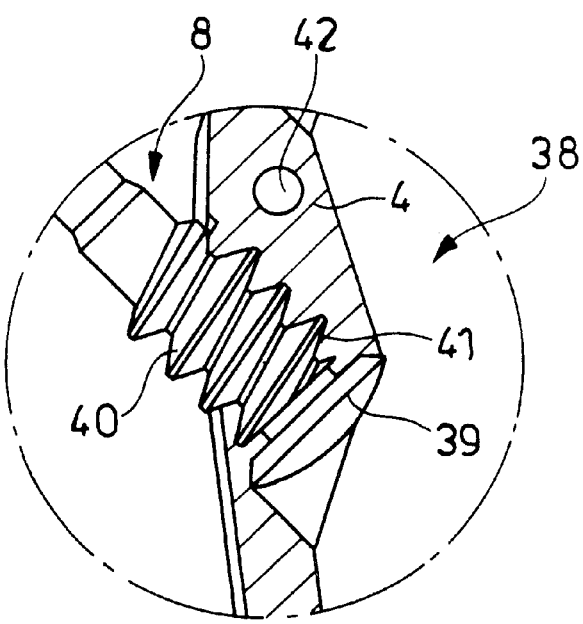
Figure 6:
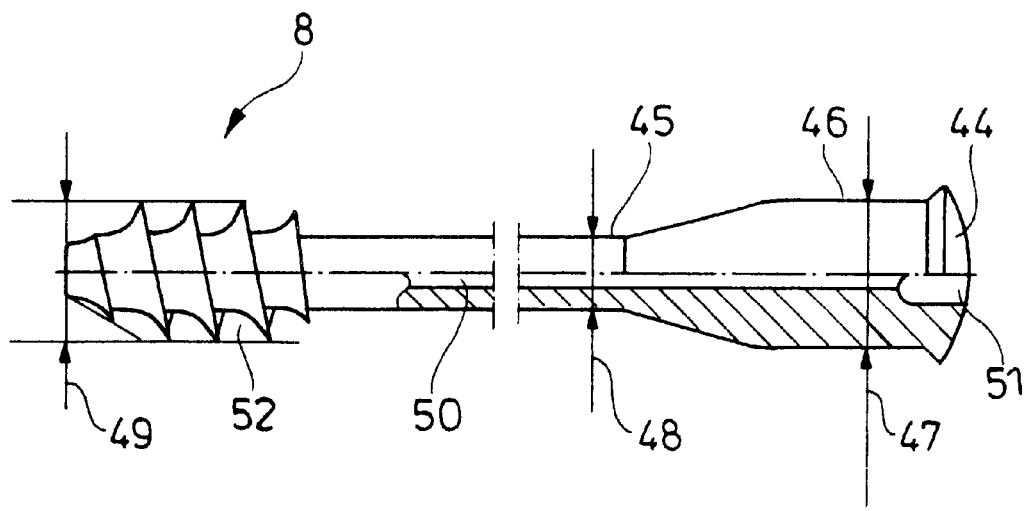
Figure 7:
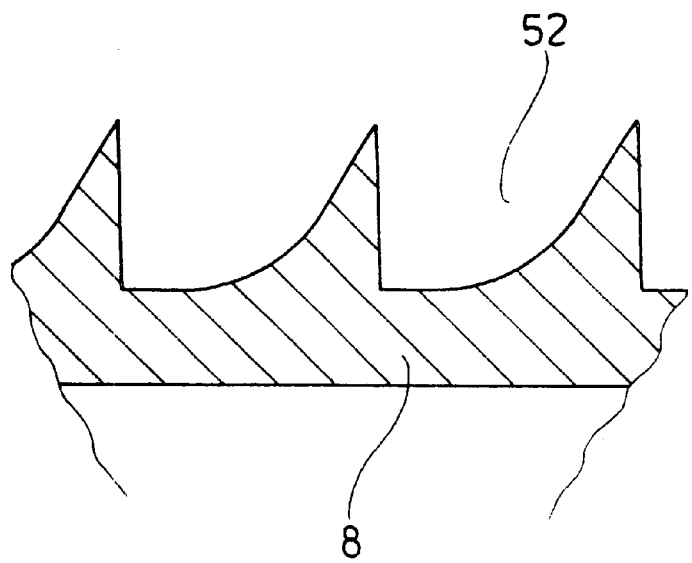
Figure 8:
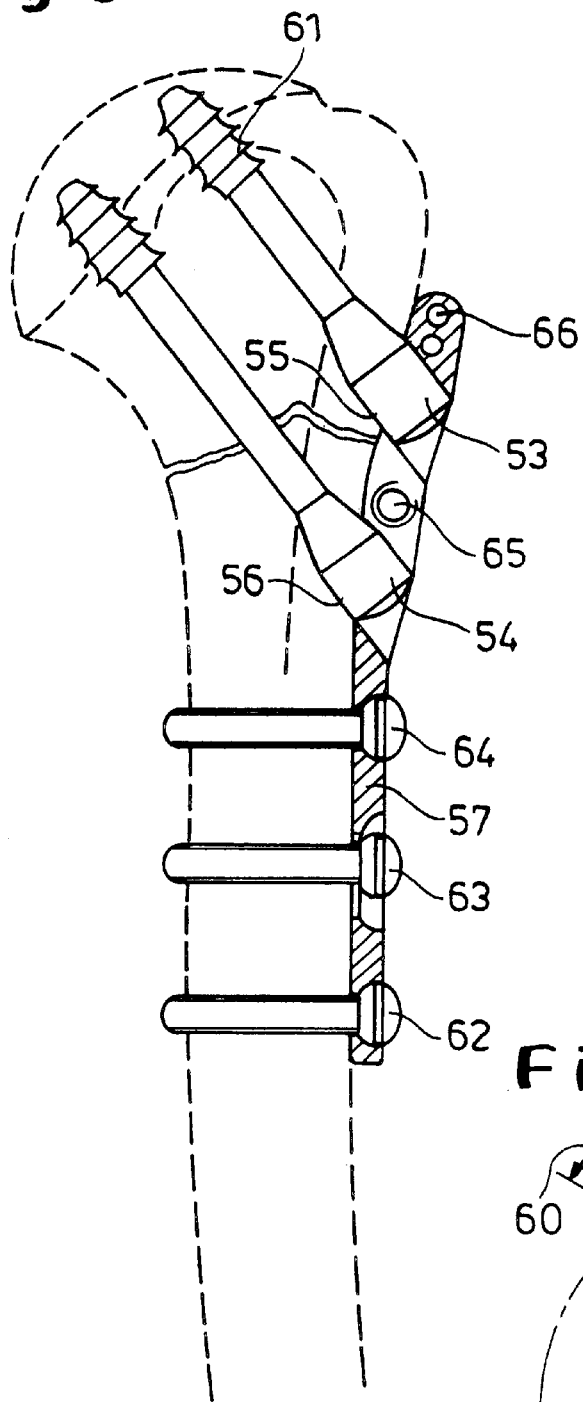
Figure 9:
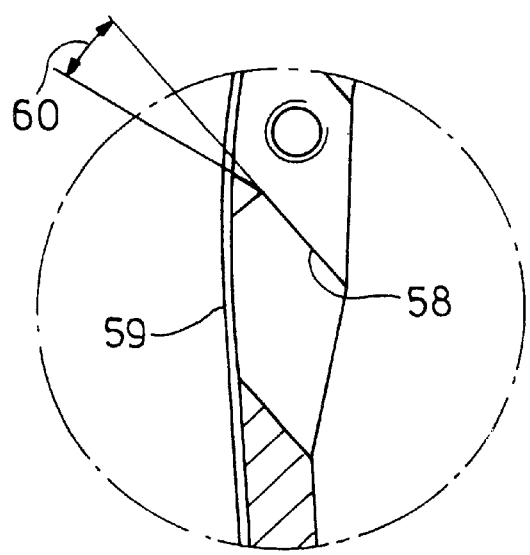

Different configuration examples of the invention are illustrated in the drawing and are described in more detail in the following:

FIG. 1 shows a long-section through the plate attached with screws to the humerus bone, FIG. 2 shows several views of the exposed plate with a clamping jaw screw, FIG. 3 shows the positioning of the clamping jaw screw in detail, FIG. 4 shows an alternative possibility of clamping the humerus head screw in the area of the plate rest, FIG. 5 shows a further alternative for clamping by means of a screw head thread, FIG. 6 shows a humerus head screw, FIG. 7 shows a section of the thread of the humerus head screw according to FIG. 6, FIG. 8 shows a long-section through an alternative configuration of a plate attached with screws in the humerus bone, and FIG. 9 shows a magnified detail of FIG. 8.

FIG. 1 shows a humerus bone with proximal humerus fracture, type III according to Neer. The part of the broken humerus shown consists of the humerus head 2 and the proximal section of the humerus shaft 3. The plate 4 contacts at the primal humerus and is adjusted in its shape to the anatomic conditions in the area of the proximal humerus. The overall length of the plate is 95 mm, its thickness in the range of the proximal section of the humerus shaft is 4 mm and it is strengthened to 9.5 mm in the area of the humerus head. The width of the plate is a maximum of 12 mm.

This plate is screwed in its lower section to the proximal section 3 of the humerus shaft with standard Corticalis screws 5, 6, 7. Seats for special humerus head screws 8 and 9 are provided in the upper section of the plate 4 as clamping jaws 10, which allow for a tight clamping of the humerus head screws 8, 9 into the plate 4.

FIG. 2 shows the isolated plate 4 in an illustration drawn to scale. In the lower section 11 of the plate 4 three holes 12, 13, 14 are provided in one line, of which the middle hole 13 is carried out as a long hole. These holes are designed to accommodate standard Corticalis screws 5, 6, 7. Between these holes the plate has narrowed sections 15 and 16, through which a more constant stress distribution in the plate is achieved. The contact surface 17 is not flat but designed in a concave way, by means of which the plate contacts the surface of the humerus bone better.

The lines 18 and 19 represent the visible edges of the narrowed sections 15 and 16, which are displayed due to the concave shaping of the plate. There are therefore no recesses, the plate is in contact over the whole surface.

The upper part 20 of the plate 4 shows guides 21, 22 as the seat for the humerus head screws 8 and 9. These guides are arranged at an angle 23 of 37.5° against the longitudinal axis of the humerus. This corresponds approximately with the physiological angle of the humerus head. These guides are carried out as holes, which have a larger diameter to accommodate a screw head 24 and a slightly smaller diameter to accommodate a thicker screw barrel 25. The depth of the guides 21, 22 and therefore the thickness of the plate 4 in this area is selected in such a way, that the length of the guide is just sufficient to give the screw 8 or 9 a secure hold in a pre-determined angular position.

The top view onto the upper part 20 of the plate 4 shown in FIG. 2 shows, that the plate 4 has a gap between the holes 21, 22, which serve as guides. Across this gap a hole 26 is provided, in which a clamping jaw screw 27 can be screwed.

FIG. 3 shows the clamping of the screws 8 and 9 and in particular their thicker part 25 by means of a clamping jaw device 28. By screwing the clamping jaw screws 27 into the thread of the hole 26, the parts of the plate 4, which are positioned on both sides of the gap 29, are moved towards each other, so that the gap 29 is narrowed. As a result, the cross-sections of the guides 21, 22 are also slightly deformed, so that the walls of the guides are pressed against the thicker barrel section 25 of the screws 8 or 9. As a result, the screws 8 and 9 are also attached in fixed angular position against rotation around the screw axis 30 and shifting in direction of the screw axis 30.

FIG. 4 shows an alternative clamping device 31. With this type of clamping of the humerus head screws 8 or 9 in the plate 4, the screw head 32 is slotted and provided with a conical hole 33 and a thread 34 on the inside. At the inner end of the thread 34 a hexagonal socket 35 follows in the screw, with which the screw 8 can be screwed into the humerus head. After screwing in the screw 8 the cone-shaped screw 36 is also screwed into the thread 33 of the screw 8 with a hexagonal socket 37. As a result, the slotted head 32 of the humerus head screw 8 is pressed apart and consequently clamped tightly in the plate 4.

FIG. 5 shows a further alternative of a clamping device 38. With this type of clamping, the humerus head screw 8 of the barrel next to the screw head 39 is designed as an outer thread 40 and the screw seat 41 in the plate 4, which serves as a guide, is designed as a corresponding inner thread. The clear diameter of the thread in the plate 4 is at least as large as the diameter of the Spongiosa thread of screw 8 at the end of the screw. The pitches of the screw head thread 40 and of the Spinosa thread at the end of the screw must be approximately the same, so that the humerus head screw 8 can be inserted. Furthermore, the pitch 40 must be designed in such a way that self-locking is ensured. When screwing in the humerus head screw 8 it is finally firmly tightened, by means of which a secure clamping of the humerus head screw 8 in the plate 4 is achieved.

This variation in comparison to the two variations previously described allows no or only a minimum interfragmentary compression. Therefore functionally it operates like an internal fixative of the humerus head.

Across the course of the described guides of the humerus head screws, holes 42, 43 are provided in the plate, which serve as accommodation for wire cerelages or PDS cords for re-attachment of torn out tubercula.

A screw 8, which in its design corresponds to the screw 9, except in length, is shown in FIG. 6. This screw consists of the screw head 44, the screw barrel 45 and the thread 52. The screw barrel 45 is initially cone-shaped towards the head 44, so that it becomes thicker in the area of the head 44. This thicker barrel section 46, which is provided over the distance of the barrel, has a barrel diameter 47, that is enlarged compared to the remaining barrel diameter 48. The outer diameter 49 of the thread 52 should be larger than the diameter 48 of the barrel section 45. It is, however, of the same size or smaller than the diameter 47 of the thicker barrel section 46. The screw 8 has a central hole 50, so that it can be placed over a special guidance system, and a hexagonal socket 51 for tightening the screw 8 is provided inside the screw head 44.

To allow an adjustment of the screw length required, the screw lengths of these screws are planned between 40 mm and 80 mm in intervals of 5 mm. This allows the selection of the right screw length for different fractures and different bones.

The screws have a Spongiosa thread. An illustration of such a thread is shown in FIG. 7. For the application area according to the invention not the standard screw with a Spongiosa thread of 6.5 mm but a screw with a Spongiosa thread of 8.5 mm is provided. This screw leads to significantly increased holding forces inside the bone and is therefore also suitable for use with strongly osteoporotically changed bones.

The plate design shown in FIG. 8 conforms essentially with the plate design in FIG. 1. The plate is, however, designed significantly narrower in the area of the accommodation of the humerus head screws. The humerus head screws 53 and 54 no longer have a raised head, as shown in FIG. 1, but end with a guiding barrel 55 or 56. To afford the humerus head screw 53 or 54 a bearing surface in the plate 57, as shown in FIG. 9, the hole 58 is not continuous, but is reduced directly at the contact with the bone 59 by an angle 60 of approx. 15°.

Due to the angled position of the hole 58 in the plate 57 a "nose" is consequently created, which serves as a bearing surface for the screw 54 or the screw 53. The Spongiosa thread 61 of the humerus head screws 53 or 54 is able to either receive such a small outer diameter, that it can also be inserted through the narrowed hole 58, or the "nose" and Spongiosa thread are matched in such a way that the humerus head screw can be screwed into the narrowed section of the hole 58 without a problem.

As a result of this preferred configuration the plate 57 is to be designed narrower by approx. 25% to 30% than the plate 4. Its maximum width is only 7 mm. Compared to this the Corticalis screws 62, 63, 64 in the shaft area of the plate 57 increase by approx. 6 mm.

Conditional to the design, the thread of the clamping jaw screw 65 was reduced from M5 to M4 and the hole 66 for accommodating a PDS cord or a wire moved to the upper end of the plate 57.

What is claimed is:

1. An implant for stabilization of a fracture of the humerus in the area of the humerus head with or without cooperation of the tubercula with a plate (4), in which holes (12, 13, 14) for screws (5, 6, 7) are arranged, wherein the plate provides at least one guide for a humerus head screw having a screw barrel, which holds the humerus head screw in a stable way at an angle against the plate, wherein the plate (4) provides a clamping device (28, 31, 38), which holds the humerus head screw in a stable way against a shift in direction of the screw barrel.

2. An implant according to claim 1, further comprising at least two humerus head screws and at least two guides (21, 22) comprising holes, whose cross-sections correspond with a barrel diameter (47) of the humerus head screws (8, 9).

3. An implant according to claim 2 wherein the plate provides as a clamping device a gap (29) with a cross hole (26) between the guides for the humerus head screws (8, 9).

4. An implant according to claim 2 wherein the axes of the guides for the humerus head screws (8, 9) are in a single plane with the longitudinal axis of the humerus shaft.

5. An implant according to claim 1, wherein the angle (2, 3) is between 35° and 40°.

6. The implant according to claim 5 wherein the angle is 37.5°.

7. An implant according to claim 1, characterized in that the plate (4) provides holes (42, 43) running parallel to its upper and lower side.

8. An implant according to claim 1, characterized in that the plate (4) has a maximum thickness of approx. 6 to 8 mm.

9. An implant according to claim 1, characterized in that the plate (4) has a maximum width of 12 mm.

10. An implant according to claim 1, the plate (4) provides guides (21, 22) for two humerus head screws (8, 9).

11. The implant according to claim 1 wherein the angle is device is removable.

* * * * *